United States Patent

Yoon et al.

[11] Patent Number: 5,882,932
[45] Date of Patent: Mar. 16, 1999

[54] CONTINUOUS QUICK MEASUREMENT OF BIOCHEMICAL OXYGEN DEMAND AND APPARATUS

[75] Inventors: Kyung Shick Yoon; Yong Seok Park; Hyung Charn Kim; Yong Teak Yi; Yeal Soon Hwang, all of Taejon; Sung Yoon Kang; Ki Nom Chung, both of Seoul; Jin Cheol Kim, Goyang, all of Rep. of Korea

[73] Assignee: Yukong Limited, Seoul, Rep. of Korea

[21] Appl. No.: 927,562

[22] Filed: Sep. 8, 1997

[30] Foreign Application Priority Data

Sep. 10, 1996 [KR] Rep. of Korea .................... 96-39431

[51] Int. Cl.$^6$ .................................................. G01N 33/18
[52] U.S. Cl. ................... 436/62; 436/138; 435/286.1; 435/286.5; 435/287.1
[58] Field of Search ................... 422/79; 436/50, 436/52, 62, 138; 435/3, 29, 286.1, 286.5, 287.1

[56] References Cited

U.S. PATENT DOCUMENTS

| | | |
|---|---|---|
| 4,898,829 | 2/1990 | Siepmann et al. ............ 435/289 |
| 5,281,537 | 1/1994 | Robertson et al. ............ 436/62 |
| 5,356,792 | 10/1994 | Maeda et al. ............ 435/29 |
| 5,702,951 | 12/1997 | Bridger ............ 436/62 |

*Primary Examiner*—David A. Redding
*Attorney, Agent, or Firm*—Seidel, Gonda, Lavorgna & Monaco, PC

[57] ABSTRACT

A continuous, quick measurement method of BOD, and an apparatus therefor is disclosed. The apparatus comprises a sample tank in which a sample is prepared suitably for the measurement, a reactor in which microorganisms maintain their activity, a medium reservoir which contains nutrients for the growth of the microorganisms, pumps for transferring liquids, and a microprocessor which controls the operation of all means including a magnetic stirrer for mixing the liquid in the reactor and diagnoses of the apparatus itself. Using the apparatus, the method comprises a continuous culture stage, an endogenous respiration stage, a endogenous respiration rate-measuring stage, a sample feeding stage and a BODq measuring stage. The apparatus can detect BOD in one hour and is very low in error rate. Further, because microorganisms can be continuously cultured, the apparatus is semi-permanent, easy to manage, low in cost and suitable to be operated at a treatment site.

10 Claims, 7 Drawing Sheets

CONTINUOUS QUICK MEASUREMENT OF BIOCHEMICAL OXYGEN DEMAND AND APPARATUS

BACKGROUND OF THE INVENTION

1. Field of the Invention

The present invention relates, in general, to a method for measuring biological oxygen demand (hereinafter referred to as "BOD") continuously and rapidly, and an apparatus therefor. More particularly, the present invention relates to a method with which BOD can be automatically measured in 20 min by using the apparatus.

2. Description of the Prior Art

BOD refers to the oxygen amount required to oxidize the organic materials which can be decomposed by the metabolic action of aerobic microorganisms. Because BOD is indicative of the amount of the organic material present in a solution, BOD is one of the most important indicators for water pollution and has the following implications.

When sewage or waste water is discharged from homes or plants to a river, the organic materials contained therein are primarily decomposed by the aerobic microorganisms which inhabit the river. Owing to this, the dissolved oxygen in the river is exhausted, thereby creating an environment in which it is very difficult for higher aerobic organisms, such as fish, to survive.

Thus, the BOD of sewage or waste water is indicative of the concentration of the organic materials it contains, and the influence of the sewage or waste water on the environment. Most countries of the world have their own BOD allowance limits in order to protect their own environments.

To reduce the deleterious influence of waste water, the organic materials in the waste water should be removed prior to being discharged into the environment. One method is to biologically treat the waste water. In fact, most home sewage and plant waste water is processed by such a biological treatment method.

According to this treatment method, the organic materials in waste water are decomposed by a high concentration of aerobic microorganisms (active sludge), prior to being discharged into the environment. This is based on the strategy that a phenomenon occurring in nature is intensively and rapidly utilized at a safe site before the sewage or waste water is discharged into the environment.

In running a process for the biological treatment of waste water, the BOD of an influx and the BOD in an aeration bath are very important parameters to normally run the process and to prevent various problems which may occur in the process. Further, because the BOD of an efflux, as mentioned above, is legally regulated, it is continuously measured and managed.

Therefore, in order to meet legal regulations or in order to smoothly run the biological treatment process, the BOD of waste water should be measured.

Conventionally, the measurement result is completely interpreted 5 days after measurements are taken. This delay hinders the application of the BOD result to waste water treatment process management. The delay also makes the BOD result unreliable in legally regulating the waste water of a plant.

There is a standard for BOD measurement in each country. For example, such standards include American Public Health Association Standard Method No. 219 in the U.S.A., Japanese Industrial Standard JIS K0102-1974 in Japan, and KS M0111 #19 in Korea. These three are almost the same in practice and all of them give complete interpretation of BOD 5 days after BOD measurement. In addition, because these measurement processes are very difficult and complicated, the BOD results are modulated somewhat, depending on the skill of the experiment workers. Further, even though skilled workers measure BOD, the results are not good in reproducibility.

With increasing interest in the environment, a new BOD measurement method that is fast, correct and displays good reproducibility is desperately required.

Up to now, much effort has been made to solve the problems of conventional BOD measurement techniques. For example, U.S. Pat. No. 4,350,763 to Shuichi Suzuki (hereinafter referred to as "'763 patent") suggests a quick method by which BOD can be measured in 30 min. The quick BOD measurement of the '763 patent has a significant advantage of being quicker and simpler than a conventional BOD measurement (hereinafter referred to as "BOD5"). According to the '763 patent, microorganisms are immobilized on a dissolved oxygen (hereinafter referred to as "DO") sensor membrane. In solutions free of organic material, constant DO values are read by their action. When a solution at a constant flow rate and containing organic material comes into contact with the immobilized microorganisms, the microorganisms use the dissolved oxygen to decompose the organic material. The DO value decreases with the concentration of the contained organic material. In other words, '763 patent takes advantage of the fact that the concentration of organic material in a sample is proportional to $\Delta DO$ (difference in DO between an organic material-free buffer solution and a sample).

The immobilized-microorganism sensor of '763 patent is advantageous in that it is simple, but it has the following disadvantages:

First, because the activity of the microorganisms immobilized on the DO sensor membrane changes with time, frequent reference to a standard solution (defined in BOD) should be made in order to detect the $\Delta DO$, thereby calculating the BOD.

Second, measurement itself is impossible unless the organic material in the sample is decomposed by the microorganisms. This phenomenon occasionally occurs in the waste water from plants.

Third, when the concentration of the organic material in a sample exceeds a certain degree, the oxygen consumption rate of the microorganisms does not increase any more. In such case, the concentrated sample should be diluted to a concentration at which the organic material concentration and the oxygen consumption rate are in a proportional relation, in order to be able to measure the BOD of the sample.

Another prior technique is disclosed in U.S. Pat. No. 4,898,829 to Friedrich W. Siepmann (hereinafter referred to as the "'829 patent") which complements the above-noted disadvantages of the '763 patent. According to the '829 patent, carriers on which microorganisms are immobilized are placed in a reactor into which test water continuously flows, so that the microorganisms capable of decomposing the organic materials in the test water naturally adhere to the carriers and grow therein. This addresses a disadvantage of the '763 patent—the indecomposibility of organic material.

The '829 patent is similar to the '763 patent in measurement principle but significantly different in working mechanism. In accordance with the '829 patent, a sample is aerated to have a saturated DO concentration at a certain temperature and then fed into a reactor. As in the '763 patent, the oxygen consumption rate of the microorganisms changes with the concentration of the organic materials in the sample, so that the sample which is passing through the reactor comes to have a different DO.

To avoid the dilution problem of the '763 patent, the '829 patent suggests an apparatus equipped with a diluting water line with which the sample passing through the reactor has a constantly maintained ΔDO (difference in DO between at the inlet and at the outlet of the bath). When the BOD of a sample is too high, the DO is considerably decreased, which can be compensated for by adding a great amount of diluting water to the sample. On the other hand, a smaller BOD is attributed to a low decrease of DO, which requires the addition of a small amount of diluting water.

The apparatus of the '829 patent further comprises a microprocessor with which the flow rates of the diluting water and the sample are controlled, thereby calculating the BOD of the sample.

The '829 patent is a considerably advanced technique capable of solving the problems of '763 patent including: 1) indecomposibility of organic material, 2) dilution of sample, and 3) maintenance in the activity of immobilized microorganisms, as well as automatic measurement of BOD. The '829 patent is still limited by the following:

First, when the sample has a low concentration of organic material, there are not enough nutrients to grow the microorganisms adherent to the carriers, so that immobilized microorganisms are not maintained to the degree of being able to measure BOD.

Second, because the activity of the microorganisms has a great influence, as in the '763 patent, the activity should be constantly maintained. Following the installation of the apparatus, a waiting period should be given until the microorganisms of the carriers reach a steady state. As such, it takes a long time to become ready to measure the BOD of a sample.

Third, the measurement method should be of a continuous type requiring continuous inflow of test water. Because the flow rates of the sample and the diluting water are controlled with maintenance of constant delta DO, it is impossible to apply a laboratory scale measuring apparatus other than a continuous measuring apparatus working at the site.

SUMMARY OF THE INVENTION

As mentioned above, the prior patents attempted to quickly and correctly measure BOD, but they include many problems to be solved in principle.

Based on the principle disclosed in Korean Pat. Appl. No. 93-6458 to the inventors, a BOD measuring method and apparatus therefor is developed with which BOD is measured automatically, quickly and continuously.

Therefore, it is an object of the present invention to overcome the above problems encountered in prior arts and to provide a novel, quick, continuous BOD measuring method and an apparatus therefor.

BRIEF DESCRIPTION OF THE DRAWINGS

Other objects and aspects of the invention will become apparent from the following description of embodiments with reference to the accompanying drawings in which.

DETAILED DESCRIPTION OF THE INVENTION

The reason why it takes five days for the conventional methods to measure BOD is that the amount of the aerobic microorganisms working at the initial stage of measurement are too small to rapidly decompose all the organic materials contained in a sample.

To avoid such time consuming experiments, the '763 patent and the '829 patent take advantage of the proportional relationship between the oxygen consumption rate of microorganisms and the organic material concentration in a sample, to estimate the BOD. On the other hand, the principle of the invention is not based on the increase of the oxygen consumption rate with sample concentration but on the increase of the oxygen amount consumed, like that of BOD5. Merely, instead of seeding microorganisms in the sample, a sample is added to a microorganism solution, to reduce the measurement time which it takes to measure. Presently, the measurement is possible only when the microorganism solution to be applied is in an endogenous respiration state because the change in the oxygen amount consumed depends on the concentration of the organic material in the added sample when the available organic material in the microorganism solution are completely exhausted.

The invention is similar to the above-cited patent application to the inventors in principle but different and improved in the following points:

First, the continuous apparatus of the invention can automatically run the whole procedure including sampling, quick measurement of BOD, and after measurement drainage, as well as providing for continuous repetition of the procedure.

Second, the invention can continuously culture the measuring microorganisms by use of additional nutrients and the sample taken from the spot, so that it can be applied to industrial wastewater treatment plants without biological treatment facilities, and to rivers.

Third, in the case where the discharge water passing through active sludge has a BOD5 of 10 ppm or less by virtue of good biological waste water treatment, the quick BOD of the discharge water cannot occasionally be detected with the active sludge of the treatment site (the organic material contained in the discharge water which has been treated with active sludge are believed not to be decomposed by the active sludge any more); a principle of the invention is the continuous culturing of microorganisms in the reactor by use of the sample (discharge water). Because the microorganisms grow to decompose the organic materials contained in the discharge water, the quick BOD measurement of discharge water is possible.

Figure 1:
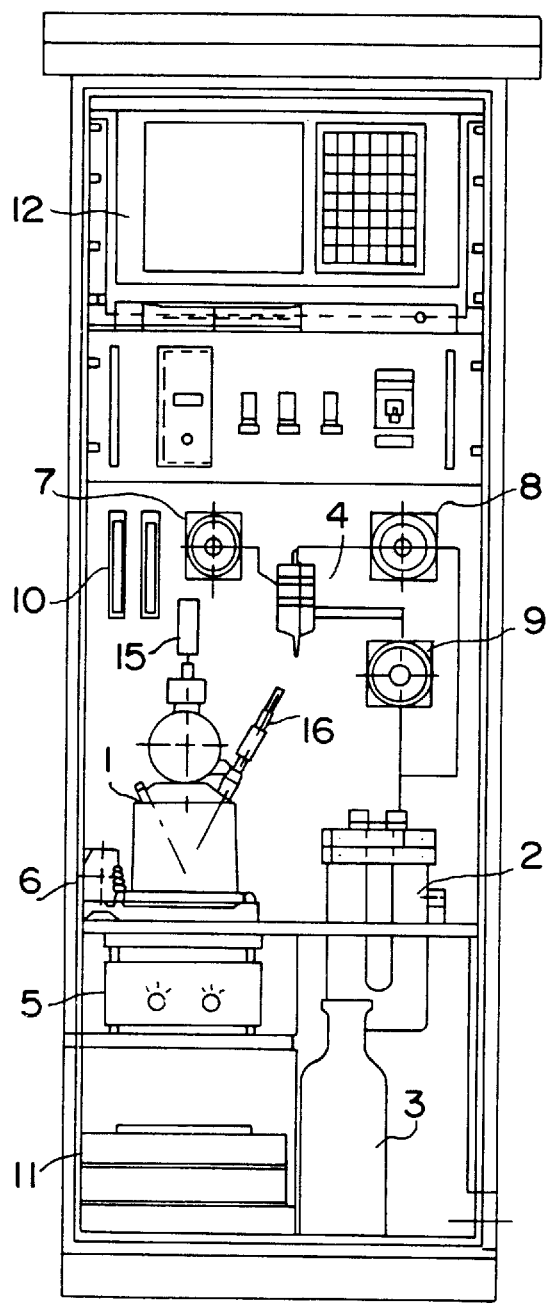
FIG. 1 schematically shows an apparatus according to the present invention.
Figure 2:
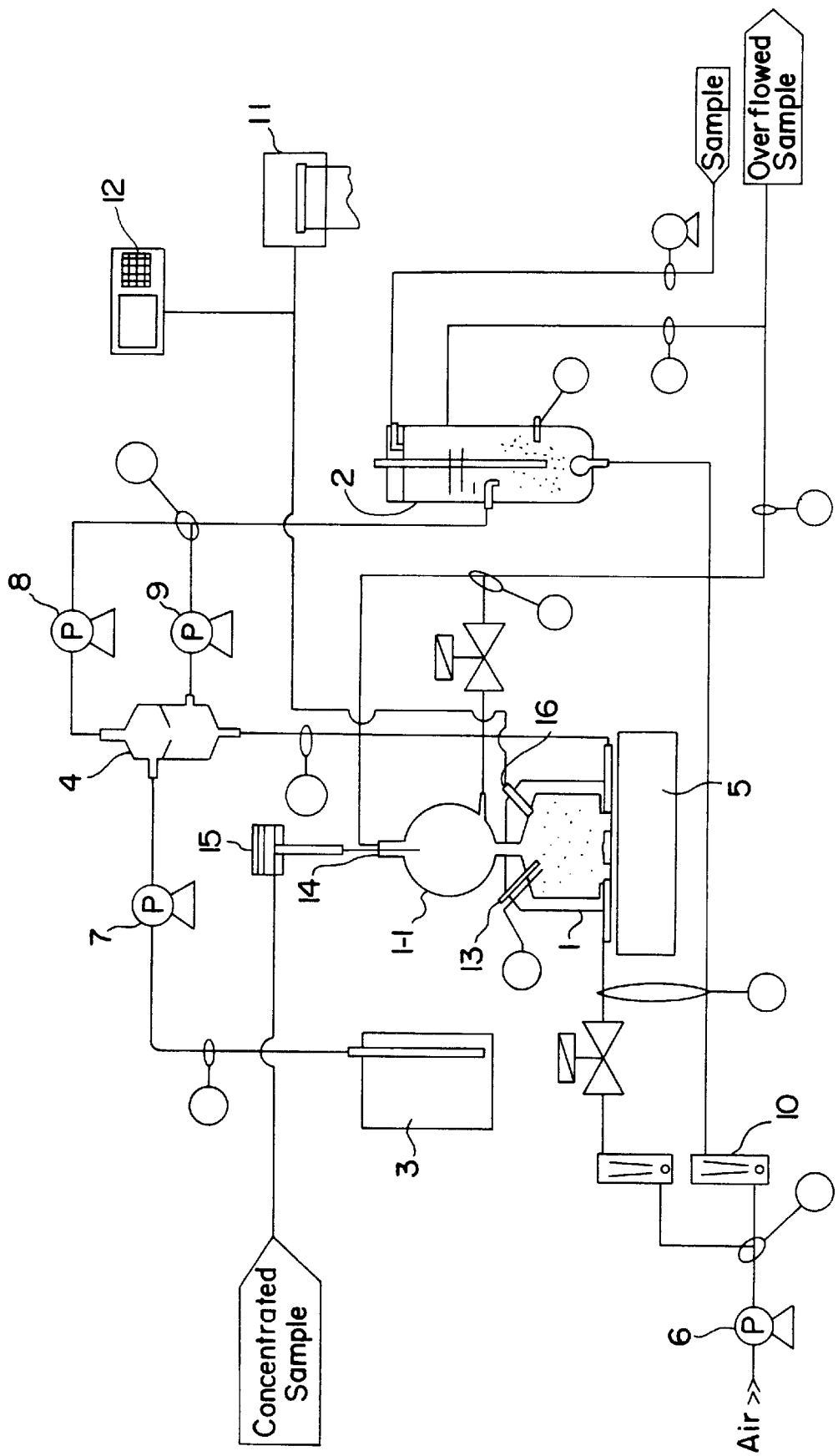
FIG. 2 is a flow diagram showing the procedure of the present invention.

Referring to FIGS. 1 and 2, there is shown a BOD measuring apparatus manufactured according to the principle of the present invention. As seen, the apparatus includes the following.

(1) A reactor 1 on a magnetic stirrer 5, which is equipped with a temperature/DO sensor 16 and a heater 13 at its upper part. The reactor is provided with two holes at its bottom and contains microorganisms capable of decomposing organic materials, one of said holes serving as an inlet through which air is influxed into said reactor 1 by the action of an air pump 6 and the other as an inlet through a sample water fed into the reactor 1.

(2) A sample tank 2, having a short tube at an upper part, through which diluted sample water flows into the sample tank 2, an overflow hole at its side for maintaining the water level of the sample, and an air conduit at the bottom of the sample tank for introducing air from the air pump 6.

(3) A medium reservoir 3, which stores the nutrients necessary for the growth of the microorganisms contained in the reactor 1.

(4) A mixing bottle 4 for mixing the sample water and the medium. The mixing bottle has a conduit at its side for introducing the medium from the medium reservoir 3 by the action of a medium pump 7, during the culture period. The mixing bottle also has a conduit at its side for introducing the sample from the sample tank 2 by the action of a sample pump 9 during the measurement period. There is a conduit on the mixing bottle at its upper part for introducing the sample from the sample tank 2 by the action of a feeding pump 8 during the culture period. At the bottom part of the mixing bottle is a discharge tube for discharging the influxes of the mixing bottle 4 into the reactor 1.

(5) An upper reaction bottle 1—1 having a neck at its bottom for connecting with the reactor 1, a hole with a cap at its upper part, and a hole at its side for draining the sample introduced from the bottom. The cap is provided with a level sensor 14, an air hole, and an inlet through which a concentrated sample flows via a syringe pump.

(6) A microprocessor 12 controls all the operations necessary for automatic measurement.

The reactor 1 is one liter in volume and contains porous carriers therein which provide a suitable habitat for microorganisms. Nutrients may be separately added to the reactor 1. At its upper part, the reactor has a neck 30 mm in diameter through which the upper reaction bottle 1—1 (350 mL in volume) is connected with the reactor 1.

Within the lower neck of the upper reaction bottle 1—1, a helical baffle is provided in order for liquid to easily move between the reactor 1 and the upper reaction bottle 1—1.

A glass tube with a diameter of 12 mm, in which many pores 3.5 mm in diameter are present, is horizontally inserted through the draining hole into the upper reaction bottle 1—1, in order to prevent the carriers from losing and clogging the draining hole.

The sample tank 2 has a volume of about 500 ml and is provided with a temperature sensor and a heater to control the temperature of the sample. A porous stone is placed in the sample tank 2. The stone spouts air introduced from the bottom of the bath 2. As mentioned above, sample water having a low concentration of organinc material (discharge water from the working spot) is introduced at a flow rate of 3 liter/h into the sample tank through the short tube. Because the overflow hole serves to maintain the residence time of the sample within 10 min., the sample in the sample tank 2 is always kept fresh.

The mixing bottle 4 is about 100 mL in volume.

The microprocessor 12 controls the automatic measurement, including, for example, the following operations: the power (ON/OFF) of the magnetic stirrer 5 and its stirring rate; the opening and shutting of the draining valve of the upper reaction bottle 1—1; the temperatures in the reactor 1 and the sample tank 2; the speed of the sample pump under the level sensor 14; the power ON/OFF of various pumps (medium pump, feeding pump, sample pump, syringe pump) and their speeds; printer 11; and the power ON/OFF of the air pump 6 and the opening and shutting of its valve.

The sequence of the whole measuring procedure is as follows:

1. continuous culture stage: continuously culturing the microorganisms in a mixture of the sample and the medium in the reactor.
2. endogenous respiration stage: continuously aerating the reactor to deplete the available organic materials therein without further introducing the sample and medium.
3. endogenous respiration rate-measuring stage: measuring the oxygen consumption rate (endogenous respiration rate) when the microorganisms are in the state of endogenous respiration that results from the depletion of the available organic materials in the reactor and cessation of the aeration.
4. Sample-feeding stage: feeding a desired amount of the sample from the sample tank to the reactor.
5. BODq-measuring stage: measuring the oxygen consumption amount increased by the feeding of the sample while the microorganisms completely decompose the organic materials within the sample fed.

Therefore, the present invention provides a continuous, quick measuring method of BOD comprising the steps of:

i) continuously culturing microorganisms in the reactor 1 by introducing a mixture of a medium containing nutrients necessary for the growth of the microorganisms and sample water from a mixing bottle 4 to the reactor at a flow rate controlled by the microprocessor;

ii) depleting all the organic materials available in the reactor 1 by aerating the reactor without further introducing the medium and the sample;

iii) measuring the endogenous respiration speed of the microorganisms which are in an endogenous respiration state owing to the depletion of the organic materials available;

iv) feeding the sample from the sample tank 2 to the reactor 1; and v) measuring the oxygen amount consumed by the microorganisms while they completely decompose the organic materials contained in the sample fed.

The following table briefly shows the operations occurring in the apparatus of the invention in accordance with the working order of the method steps.

| Order | Operation | Pf | Pm | Ps | A | Vd | St | Vol. |
|---|---|---|---|---|---|---|---|---|
| 1 | Continuous Culture | O | O | X | O | O | X | 1,000 |
| 2 | Endogenous Res. | X | X | X | O | O | O | 1,000 |
| 3 | Endo. Res. Rate-Measuring | X | X | X | X | O | O | 1,000 |
| 4 | Sample Feeding | X | X | O | X | X | O | +Vs |
| 5 | BODq Measuring | X | X | X | X | X | O | +Vs |
| 1 | Continuous Culture | O | O | X | O | O | X | 1,000 |

*Where:
Pf: Feeding Pump,
Pm: Medium Pump,
Ps: Sample Pump
A: Aeration of Reactor tank,
Vd: Drain Valve of Reactor tank,
St: Stirring, and
Vs: Volume of sample The above procedure is described below in conjunction with FIG. 2.

A sample from the treatment site, as shown in FIG. 2, flows into the sample tank 2. The sample tank 2 has an overflow hole through which some sample is directed, so that the sample tank 2 always contains fresh sample.

During the residence time in the sample tank 2, the sample is sufficiently heated to the same temperature of the reactor 1 and aerated so as to keep a saturated oxygen concentration.

Then, the sample, having a controlled temperature and oxygen concentration, is fed at a constant flow rate into the mixing bottle 4 by the feeding pump 8, in which the sample is mixed with the medium introduced from the medium reservoir 3. Thereafter, the mix flows into the reactor 1 and continuously leaves the reactor via the drain hole.

When the microorganisms start to enter an endogenous respiration stage, the feeding pump and the medium pump cease functioning while the reactor 1 is continuously aerated so that the microorganisms deplete all the organic materials available in the reactor.

Detection of almost little increase of DO value following a smooth increase means that the organic materials are depleted in the reactor and thus, the microorganisms are in the midst of an endogenous respiration stage. At this time, the oxygen consumption rate of the microorganisms is measured without further aeration, but with continuous stirring.

If the oxygen consumption rate is constant, the drain valve of the upper reaction bottle is closed and then, the sample pump 9 starts to work to introduce the sample from the sample tank 2 into the reactor 1.

In the BODq-measuring stage, the sample pump 9 ceases to function. BODq measurement is conducted by detecting the point in time at which the oxygen consumption rate (increased by the sample feeding) becomes the same as that prior to the sample feeding.

Subsequent to the completion of the BODq measurement, the process returns to the continuous culture stage, in which the drain valve is opened, the aeration starts, the stirring ceases, and the feeding pump 8 and the medium pump 7 are operated to provide fresh nutrients for the microorganisms of the reactor 1.

It is apparent from the above illustration that the present invention solves the problem of the two conventional techniques previously mentioned. That is, a change in the activity of microorganisms has an influence on the measurement result. Since the present invention measures the oxygen consumption amount increased by the addition of sample, rather than the oxygen consumption rate increasing by the addition of sample, the change in activity of microorganisms, although it may occur, does not significantly affect the BOD.

Even though the concentration of sample is low, it does not affect the growth and the maintenance of microorganisms because nutrients are separately fed and thus the present invention can be adapted to the case of a low concentration of sample. It is another advantage that the concentration range of sample which can be measured without using additional diluent or buffer is very wide, from 1 to 5,000 mg/L and the maintenance of the apparatus is very easy. Such a wide range of measurable concentrations arises from the principle of the present invention that BOD can be measured by merely changing the amount of the sample added in the reactor.

The apparatus of the invention can feed controlled amounts of sample in accordance with the following mechanism. Prior to feeding the sample (that is, in the continuous culture stage and the endogenous respiration stage), a constant water level is maintained in the reactor and the upper reaction bottle. (The flow rate which the sample pump 9 provides can be calculated). Because the sample pump 9 is operated at a constant speed, and the time which is taken to fill the upper reaction bottle 1—1 full can be measured with the aid of the level sensor provided on the upper reaction bottle 1—1. On the basis of this data, the sample pump 9 is operated for a time necessary to feed a desired amount of sample.

Further, the apparatus of the invention can automatically determine the change in the amount of sample.

For example, after an operator inputs 2 mg BOD/L as an object value of sample concentration in the reactor and 1–3 mg BOD/L as an allowance range, if the BODq of the sample is 50 ppm when the volume of the reactor and the sample amounts are 1 L and 100 mL, respectively, the sample concentration in the reactor is calculated as follows:

$$50 \text{ ppm} \times \frac{100}{1000 + 100} = 4.55 \text{ mg} \cdot BOD/L$$

Because this value is over the allowance range input, the apparatus automatically adjusts the sample amount according to the following equation:

$$50 \times \frac{\text{Sample Amount}}{1000 + \text{Sample Amount}} = 2.0 \text{ mg} \cdot BOD/L$$

Therefore, the sample amount is automatically converted to 41.7 ml.

A better understanding of the present invention may be obtained in light of following examples which are set forth to illustrate, but are not to be construed to limit, the present invention.

EXAMPLE I

The apparatus of FIG. 1 was installed at a discharging outlet of a research center's waste water treatment plant. Twenty-four hours before the installation, about 400 ml of carriers with a uniform size of 5×5×5 mm$^3$ was poured in a 2 liter beaker which contained the following components: yeast extract 5 g; glucose 5 g; sucrose 5 g; activated sludge 100 ml; and water 1 liter. Under aeration, microorganisms were cultured and immobilized on the carriers overnight with shaking.

After the installation of the apparatus, the carriers were placed in the reactor which was then filled with discharged water from the plant. The apparatus was operated under the following conditions:

| | |
|---|---|
| Influx Speed of Discharge Water | 0.5 L/h |
| Medium Concentration | 5 g · Glucose/L |
| Flow Rate of Medium | 3.6 mL/h |
| Culture Temp. | 30.0° C. |
| Temp. of Sample tank | 30.0° C. |
| Stirring Speed | 600 rpm |
| Aerating Rate (React./Sample tank) | 0.7 L/min |
| Vol. of Reactor | 1 Liter |
| Vol. of Upper Reaction bottle | 350 mL |
| Amount of Sample fed | |
| 50–350 mL (discharged water, autocontrol, feeding pump) | |
| 0.5–10 mL (influent water, autocontrol, syringe pump) | |
| Period of Measurement | 1 hour |
| Measurement Mode | | i. alternate (odd hours for low conc./even hours for high conc).

ii. one sample only (select either high or low concentration of samples; low conc.: discharged water, fed by feeding pump; high conc.: influent water, fed by syringe pump)

To know the error rate of each of the feeding means, an experiment was repeated 10 times. A linearity experiment was performed to determine the accuracy of the sample amounts which were automatically controlled by the apparatus.

The reliability and the accuracy in sample amount are given as shown in Table 1 below.

TABLE 1

Error Rate in Feeding Sample

| | Discharge Water (ml) | | | Influent Water (ml) | | |
|---|---|---|---|---|---|---|
| Value Set No. | 280 | 150 | 50 | 10 | 5 | 1 |
| | Feeding Pump | | | Syringe Pump | | |
| 1 | 278 | 145 | 48 | 9.6 | 4.7 | 0.95 |
| 2 | 281 | 147 | 51 | 10.2 | 4.7 | 0.96 |
| 3 | 283 | 152 | 49 | 10.5 | 5.1 | 1.01 |
| 4 | 280 | 150 | 49 | 10.3 | 4.8 | 1.02 |
| 5 | 277 | 146 | 52 | 9.9 | 5.3 | 0.99 |
| 6 | 276 | 145 | 51 | 10.4 | 4.9 | 0.93 |
| 7 | 274 | 153 | 50 | 9.8 | 5.1 | 1.05 |
| 8 | 279 | 152 | 47 | 9.5 | 4.9 | 1.06 |
| 9 | 285 | 148 | 52 | 9.9 | 4.6 | 0.95 |
| 10 | 278 | 146 | 49 | 10.4 | 4.8 | 0.96 |
| Average | 279.1 | 148.4 | 49.8 | 10.1 | 4.89 | 0.99 |
| Deviation | 3.28 | 3.10 | 1.69 | 0.36 | 0.22 | 0.05 |
| Error Rate | 1.18 | 2.09 | 3.39 | 3.55 | 4.46 | 4.57 |
| Accuracy | 99.7 | 98.9 | 99.6 | 100.5 | 97.8 | 98.8 |

*Error Rate: (Deviation/Average) × 100%
Accuracy: (Average/Value set) × 100%

As emplified in Table 1, the error rate in feeding sample and the accuracy of sample amount were within 5% and in the range of 97.8–100.5% over all experiments. Thus, the auto-control of the apparatus in sample amounts was very reliable.

The volume of each sample was calculated from the weight read on a balance on the assumption that its density might be 1.0 g/mL.

Consistent values were first obtained after 10 hours had passed from the start of the operation of the apparatus, demonstrating that the apparatus worked in a normal fashion. Early in the operation, there was a substantial tendency for very small BOD values to be measured because the microorganisms did not reach an endogenous respiration stage owing to the concentrated nutrients included in initial solution. The BOD measurement values gradually increased and finally became stable lo hours after the operation.

Figure 3:
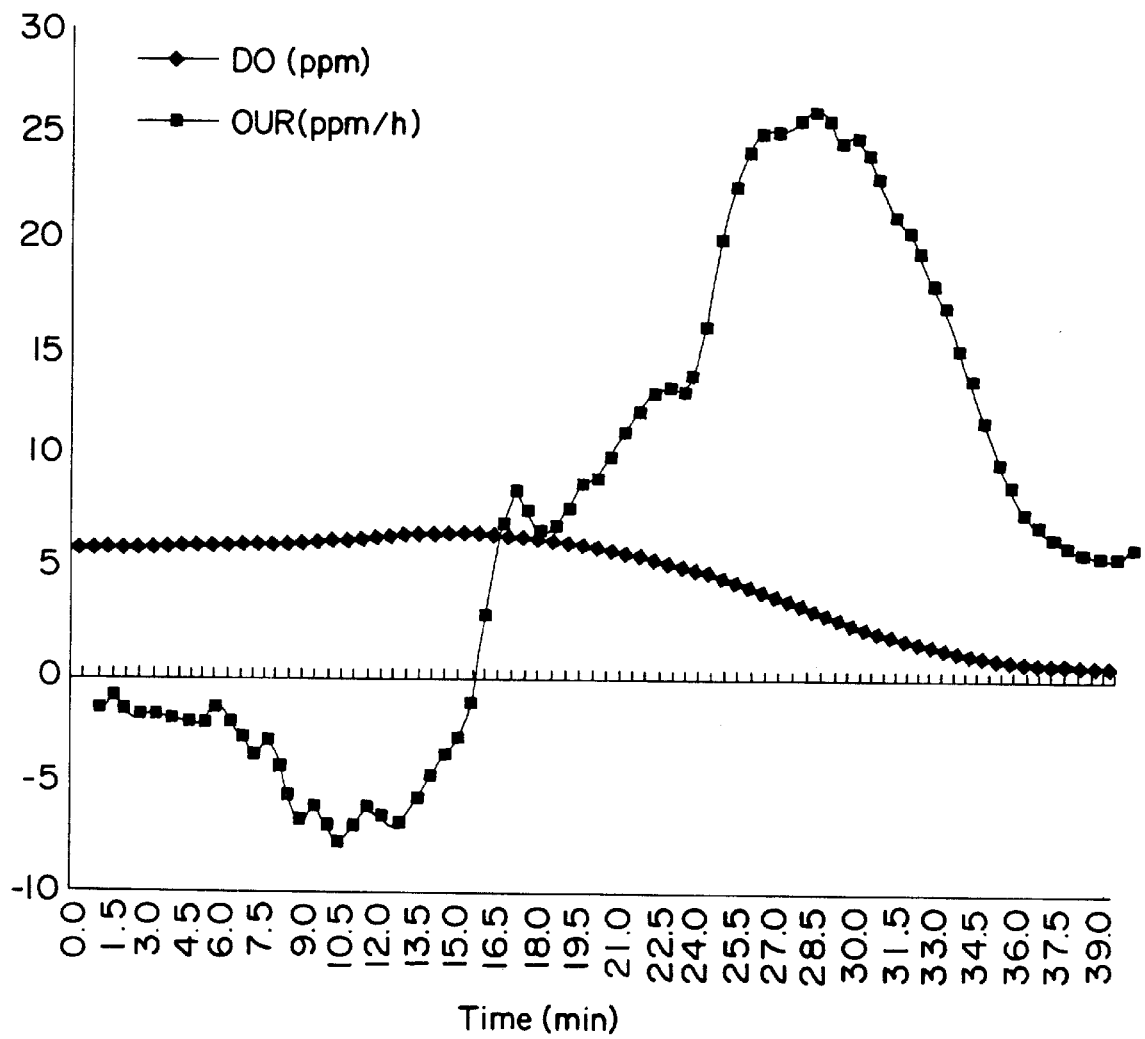
FIG. 3 is a graph showing the changes in DO and Oxygen Uptake Rate (hereinafter referred to as "OUR") according to an embodiment of the present invention.
Figure 4:
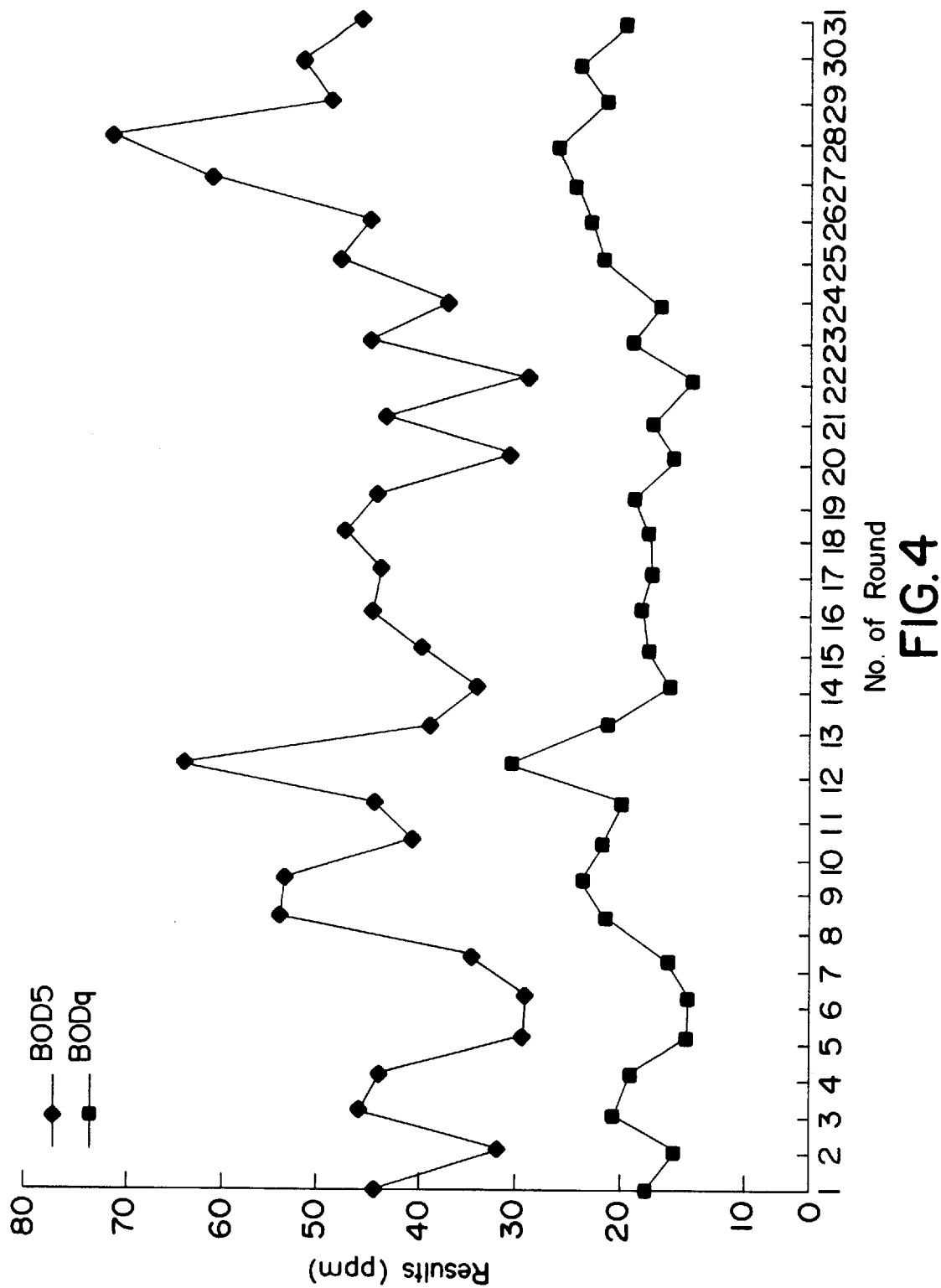
FIG. 4 is a graph showing the comparison of quick BOD (hereinafter referred to as "BODq") of the present invention with BOD5.

In order to know the changes in DO concentration and in oxygen consumption rate with time in a one measurement cycle which started at every turn of the hour sharp, measurement results of a certain hour were suggested as shown in Table 2 below and in FIG. 3.

TABLE 2

Change in DO and OUR by Measurement Stages.

| Time (min) | Do (ppm) | OUR (ppm/h) | Avg OUR (ppm/h) | Stage | Time (min) | DO (ppm) | OUR (ppm/h) | Avg OUR (ppm/h) | Stage |
|---|---|---|---|---|---|---|---|---|---|
| 0.0 | 5.841 | | | Prep. | | | | | |
| 0.5 | 5.845 | −0.48 | | for | 21.0 | 5.923 | 13.51 | 11.56 | |
| 1.0 | 5.856 | −1.32 | | Endo. | 21.5 | 5.821 | 12.24 | 12.56 | |
| 1.5 | 5.864 | −0.96 | −0.92 | Breath | 22.0 | 5.700 | 14.52 | 13.42 | |
| 2.0 | 5.879 | −1.80 | −1.36 | | 22.5 | 5.583 | 14.04 | 13.60 | |
| 2.5 | 5.898 | −2.28 | −1.68 | | 23.0 | 5.486 | 11.64 | 13.40 | |
| 3.0 | 5.903 | −0.60 | −1.56 | | 23.5 | 5.350 | 16.32 | 14.00 | |
| 3.5 | 5.920 | −2.04 | −1.64 | | 24.0 | 5.169 | 21.72 | 16.56 | |
| 4.0 | 5.947 | −3.24 | −1.96 | | 24.5 | 4.974 | 23.46 | 20.50 | |
| 4.5 | 5.956 | −1.08 | −2.12 | | 25.0 | 4.778 | 23.46 | 22.88 | Measuring |
| 5.0 | 5.974 | −2.16 | −2.16 | | 25.5 | 4.558 | 26.40 | 24.44 | BODq |
| 5.5 | 5.980 | −0.72 | −1.32 | | 26.0 | 4.338 | 26.40 | 25.42 | |
| 6.0 | 6.010 | −3.60 | −2.16 | | 26.5 | 4.143 | 23.46 | 25.42 | |
| 6.5 | 6.042 | −3.84 | −2.72 | | 27.0 | 3.923 | 26.39 | 25.42 | |
| 7.0 | 6.068 | −3.12 | −3.52 | | 27.5 | 3.690 | 27.86 | 25.90 | |
| 7.5 | 6.080 | −1.44 | −2.80 | | 28.0 | 3.483 | 24.94 | 26.40 | |
| 8.0 | 6.147 | −8.04 | −4.20 | | 28.5 | 3.275 | 24.92 | 25.91 | |
| 8.5 | 6.201 | −6.48 | −5.32 | | 29.0 | 3.067 | 24.92 | 24.93 | |
| 9.0 | 6.240 | −4.68 | −6.40 | | 29.5 | 2.847 | 26.40 | 25.42 | |
| 9.5 | 6.293 | −6.40 | −5.85 | | | | | | |
| 10.0 | 6.367 | −8.80 | −6.62 | | 30.0 | 2.664 | 22.00 | 24.44 | |
| 10.5 | 6.428 | −7.33 | −7.51 | | 30.5 | 2.481 | 22.00 | 23.46 | |
| 11.0 | 6.464 | −4.39 | −6.84 | | 31.0 | 2.310 | 20.53 | 21.51 | |
| 11.5 | 6.513 | −5.87 | −5.86 | | 31.5 | 2.138 | 20.53 | 21.02 | |
| 12.0 | 6.574 | −7.33 | −5.86 | | 32.0 | 1.980 | 19.06 | 20.04 | |
| 12.5 | 6.623 | −5.87 | −6.36 | | 32.5 | 1.845 | 16.13 | 18.57 | |
| 13.0 | 6.672 | −5.87 | −6.36 | | 33.0 | 1.699 | 17.60 | 17.60 | |
| 13.5 | 6.709 | −4.39 | −5.38 | | 33.5 | 1.589 | 13.19 | 15.64 | |
| 14.0 | 6.733 | −2.94 | −4.40 | | 34.0 | 1.491 | 11.74 | 14.18 | |
| 14.5 | 6.758 | −2.93 | −3.42 | | 34.5 | 1.393 | 11.74 | 12.22 | |
| 15.0 | 6.782 | −2.93 | −2.93 | | 35.0 | 1.332 | 7.33 | 10.27 | |
| 15.5 | 6.758 | 2.93 | −0.98 | | 35.5 | 1.259 | 8.80 | 9.29 | |
| 16.0 | 6.684 | 8.80 | 2.93 | | 36.0 | 1.198 | 7.33 | 7.82 | |
| 16.5 | 6.610 | 8.92 | 6.88 | | 36.5 | 1.149 | 5.87 | 7.33 | |

TABLE 2-continued

Change in DO and OUR by Measurement Stages.

| Time (min) | Do (ppm) | OUR (ppm/h) | Avg OUR (ppm/h) | Stage | Time (min) | DO (ppm) | OUR (ppm/h) | Avg OUR (ppm/h) | Stage |
|---|---|---|---|---|---|---|---|---|---|
| 17.0 | 6.538 | 8.68 | 8.80 | Holding | 37.0 | 1.088 | 7.33 | 6.84 | |
| 17.5 | 6.489 | 5.87 | 7.82 | Endo. | 37.5 | 1.039 | 5.87 | 6.36 | |
| 18.0 | 6.440 | 5.87 | 6.80 | Breath | 38.0 | 0.990 | 5.86 | 6.35 | |
| 18.5 | 6.367 | 8.80 | 6.84 | | 38.5 | 0.941 | 5.87 | 5.86 | |
| 19.0 | 6.293 | 8.80 | 7.82 | | 39.0 | 0.892 | 5.87 | 5.86 | |
| 19.5 | 6.212 | 9.76 | 9.12 | Feeding | 39.5 | 0.831 | 7.33 | 6.36 | Stop |
| 20.0 | 6.135 | 9.24 | 9.26 | | | | | | |
| 20.5 | 6.036 | 11.93 | 10.31 | | 40.0 | | | | Re-cuture |

BOD: 13.6 ppm
Vol. sample 340 mL
Time react: 19.5 min.

Following is the calculation for the increased oxygen consumption amount by the addition of sample (BOD).

The total oxygen consumption amount in the BODq measuring stage (the fifth stage) is the difference between the DO before the feeding of sample (19 min) and the DO at the time (38.5 min) at which the oxygen consumption rate increased by the feeding of sample returned to the microorganisms' intrinsic endogenous respiration rate. That is, 6.29−0.94=5.35 ppm.

The intrinsic oxygen amount which the microorganisms consumed owing to their endogenous respiration during the reaction time (19 to 38.5 min), is the product of the endogenous respiration rate according to the time:

$$\frac{(5.83 + 5.86)}{2} \times \frac{19.5 \text{min}}{60 \text{min}/h} = 1.90 \text{ ppm}$$

The value 5.83 ppm/h, which is referred to as "endogenous respiration rate 1", is calculated in consideration of the average oxygen consumption rate for 16–19 min (7.82 ppm/h) and the dilution effect from the sample feeding, as follows:

7.82×(1000/(1000+340))=5.83 ppm/h

The value 5.86 ppm, referred to "endogenous respiration rate 2", is one which is in the closest vicinity to the endogenous respiration rate 1, and is selected at time=38.0 min.

Then, the incremental change in oxygen consumption amount, to which the feeding of sample contributes, is calculated by subtracting the oxygen amount consumed by the intrinsic endogenous respiration of the microorganisms from the total oxygen consumption amount:

(Total ΔDO)−(ΔDO by endogenous respiration)=O.D.(Oxygen Demand)

That is, 5.35−1.90=3.4S ppm.

Therefore, the BODq of sample is obtained by multiplying the O.D. value by the dilution folds of the microorganism solution: 3.45×(1000+340)/340=13.6 ppm.

To determine the error rate of the apparatus, a test operation was continuously done for 24 hours and this process was repeated 8 times. The results are given as shown in Table 3 below.

TABLE 3

Test for Error Rate unit: ppm
No of Test

| Time | 1 | 2 | 3 | 4 | 5 | 6 | 7 | 8 |
|---|---|---|---|---|---|---|---|---|
| 1 | 20.60 | 21.60 | 17.30 | 17.70 | 8.94 | 14.25 | 5.16 | 6.14 |
| 2 | 19.30 | 22.90 | 17.70 | 19.10 | 9.61 | 13.87 | 5.14 | 5.70 |
| 3 | 19.90 | 22.70 | 15.20 | 18.50 | 9.58 | 13.99 | 6.09 | 5.84 |
| 4 | 20.20 | 22.40 | 12.50 | 19.30 | 8.35 | 14.14 | 6.13 | 6.06 |
| 5 | 19.10 | 19.50 | 14.60 | 19.30 | 8.16 | 13.90 | 5.34 | 5.68 |
| 6 | 19.90 | 19.40 | 16.80 | 17.50 | 8.80 | 13.83 | 5.90 | 4.95 |
| 7 | 21.40 | 25.60 | 18.80 | 16.90 | 7.54 | 12.34 | 5.21 | 5.04 |
| 8 | 20.80 | 20.60 | 17.90 | 17.80 | 7.76 | 12.26 | 5.62 | 5.10 |
| 9 | 19.70 | 22.70 | 16.30 | 16.90 | 7.84 | 12.37 | 4.78 | 5.00 |
| 10 | 19.70 | 23.10 | 15.60 | 16.80 | 7.63 | 12.48 | 4.76 | 5.26 |
| 11 | 19.40 | 21.60 | 15.00 | 16.40 | 7.79 | 13.00 | 5.33 | 4.92 |
| 12 | 20.30 | 25.50 | 17.20 | 16.80 | 7.90 | 12.94 | 5.99 | 5.05 |
| 13 | 18.60 | 21.70 | 18.30 | 15.90 | 7.10 | 12.53 | 6.57 | 4.96 |
| 14 | 19.80 | 22.70 | 16.20 | 16.90 | 7.59 | 13.78 | 5.46 | 4.98 |
| 15 | 18.60 | 21.30 | 15.20 | 18.40 | 7.73 | 13.44 | 5.70 | 5.13 |
| 16 | 21.40 | 21.50 | 17.40 | 21.60 | 7.62 | 12.26 | 6.21 | 4.72 |
| 17 | 17.30 | 22.60 | 14.90 | 19.80 | 7.67 | 13.32 | 5.65 | 4.61 |
| 18 | 17.70 | 21.80 | 17.90 | 20.70 | 7.38 | 13.33 | 6.81 | 4.53 |
| 19 | 18.80 | 22.80 | 13.30 | 17.60 | 6.97 | 13.52 | 5.17 | 4.89 |
| 20 | 18.80 | 19.80 | 11.60 | 16.40 | 6.97 | 13.14 | 4.37 | 4.33 |
| 21 | 19.40 | 16.80 | 18.60 | 17.40 | 6.43 | 12.61 | 5.42 | 4.26 |
| 22 | 18.90 | 19.10 | 15.50 | 17.30 | 7.55 | 13.49 | 4.75 | 4.17 |
| 23 | 20.70 | 18.40 | 17.70 | 16.00 | 6.98 | 13.12 | 4.12 | 4.69 |
| Avg. | 19.58 | 21.57 | 16.11 | 17.87 | 7.82 | 13.21 | 5.46 | 5.04 |
| Dev. | 1.05 | 2.07 | 1.92 | 1.50 | 0.80 | 0.65 | 0.67 | 0.54 |
| ER % | 5.4 | 9.6 | 11.9 | 8.4 | 10.2 | 4.9 | 12.3 | 10.7 |

Because the treatment site was a place where the process was not necessary to be operated every day, the above error rate data was obtained on the days for which the discharge water stayed in a pond.

The operation results obtained for a half-year period show that BODq ranges from 5 to 22 ppm and the error rate, which is obtained by dividing the standard deviation by the average value, is around 10%, as shown in Table 3.

To examine the correlation of the BODq, which can be detected every hour, with conventional BOD5, as well as with chemical oxygen demand (COD) and total organic carbon (TOC), discharge water was taken for a certain period and subjected to BOD5, COD, and TOC analyses.

The results are given as shown in Table 4 and in FIGS. 4 to 7. The results demonstrate that the BODq of the invention is in the highest correlation with BOD5.

TABLE 4

Operation at Treatment Site

| No. of Round | Data (ppm) BOD5 | BODq | TOC | CODcr | Comparison B5/Bq | B5/C | B5/T |
|---|---|---|---|---|---|---|---|
| 1 | 44.7 | 17.0 | 25.8 | 100.0 | 2.63 | 0.45 | 1.73 |
| 2 | 31.9 | 14.2 | 20.5 | 80.0 | 2.25 | 0.40 | 1.56 |
| 3 | 46.2 | 20.0 | 23.1 | 83.0 | 2.31 | 0.56 | 2.00 |
| 4 | 44.1 | 19.0 | 23.6 | 78.0 | 2.32 | 0.57 | 1.87 |
| 5 | 29.0 | 12.5 | 19.8 | 61.0 | 2.32 | 0.48 | 1.46 |
| 6 | 28.6 | 12.5 | 16.8 | 59.0 | 2.29 | 0.48 | 1.70 |
| 7 | 34.2 | 14.5 | 23.5 | 64.0 | 2.36 | 0.53 | 1.46 |
| 8 | 54.0 | 21.1 | 26.2 | 77.0 | 2.56 | 0.70 | 2.06 |
| 9 | 54.0 | 22.9 | 45.7 | 110.0 | 2.36 | 0.49 | 1.18 |
| 10 | 40.8 | 21.5 | 32.1 | 72.0 | 1.90 | 0.57 | 1.27 |
| 11 | 44.5 | 19.2 | 36.2 | 93.0 | 2.32 | 0.48 | 1.23 |
| 12 | 64.0 | 30.6 | 35.0 | 120.0 | 2.09 | 0.53 | 1.83 |
| 13 | 38.9 | 20.3 | 23.2 | 70.0 | 1.92 | 0.56 | 1.68 |
| 14 | 33.5 | 14.2 | 20.7 | 60.0 | 2.36 | 0.56 | 1.62 |
| 15 | 39.6 | 16.4 | 27.7 | 75.0 | 2.41 | 0.53 | 1.43 |
| 16 | 44.8 | 17.1 | 26.3 | 68.0 | 2.62 | 0.66 | 1.70 |
| 17 | 43.9 | 16.2 | 26.0 | 63.0 | 2.71 | 0.70 | 1.69 |
| 18 | 47.9 | 16.6 | 30.3 | 67.0 | 2.89 | 0.71 | 1.58 |
| 19 | 44.6 | 18.0 | 31.0 | 89.0 | 2.48 | 0.50 | 1.44 |
| 20 | 30.8 | 13.6 | 22.3 | 66.0 | 2.26 | 0.47 | 1.38 |
| 21 | 43.8 | 16.2 | 26.9 | 81.0 | 2.70 | 0.54 | 1.63 |
| 22 | 28.4 | 12.1 | 22.1 | 44.0 | 2.35 | 0.65 | 1.29 |
| 23 | 45.3 | 18.4 | 25.5 | 78.0 | 2.46 | 0.58 | 1.78 |
| 24 | 36.7 | 14.6 | 28.0 | 81.0 | 2.51 | 0.45 | 1.31 |
| 25 | 48.5 | 21.1 | 29.0 | 91.0 | 2.30 | 0.53 | 1.67 |
| 26 | 45.5 | 22.0 | 30.0 | 90.0 | 2.07 | 0.51 | 1.52 |
| 27 | 61.5 | 23.7 | 36.5 | 99.0 | 2.59 | 0.62 | 1.68 |
| 28 | 71.3 | 25.3 | 38.2 | 101.0 | 2.82 | 0.71 | 1.87 |
| 29 | 48.9 | 20.7 | 33.0 | 99.0 | 2.36 | 0.49 | 1.48 |
| 30 | 52.2 | 23.2 | 38.0 | 101.0 | 2.25 | 0.52 | 1.37 |
| 31 | 46.5 | 18.5 | 26.9 | 82.0 | 2.51 | 0.57 | 1.73 |
| Average (ppm) | | | | | 2.40 | 0.55 | 1.59 |
| Deviation (ppm) | | | | | 0.23 | 0.08 | 0.22 |
| Error Rate (%) | | | | | 9.7 | 14.9 | 14.1 |

From the above data, it is apparent that the determination of BODq has an error rate of 9.7% and can pre-estimate with higher accuracy than the other measurements (COD and TOC) which have an error rate of 14.9% and 14.1%, respectively.

Figure 5:
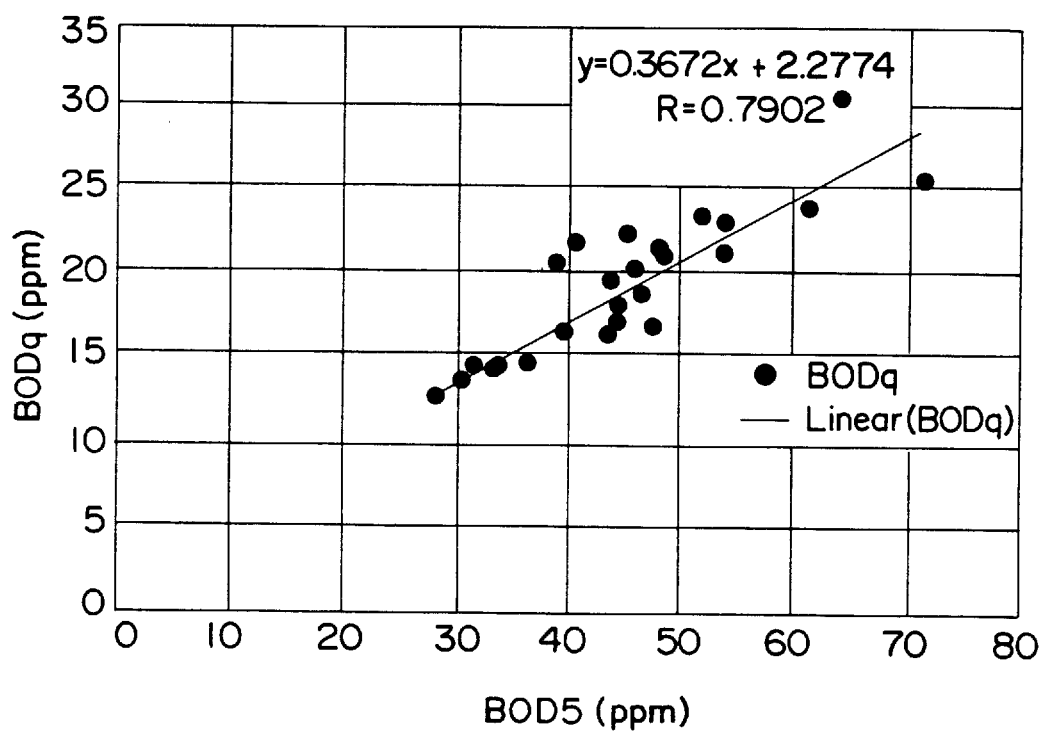
FIG. 5 is a graph showing the correlation of BODq of the present invention with BOD5.
Figure 6:
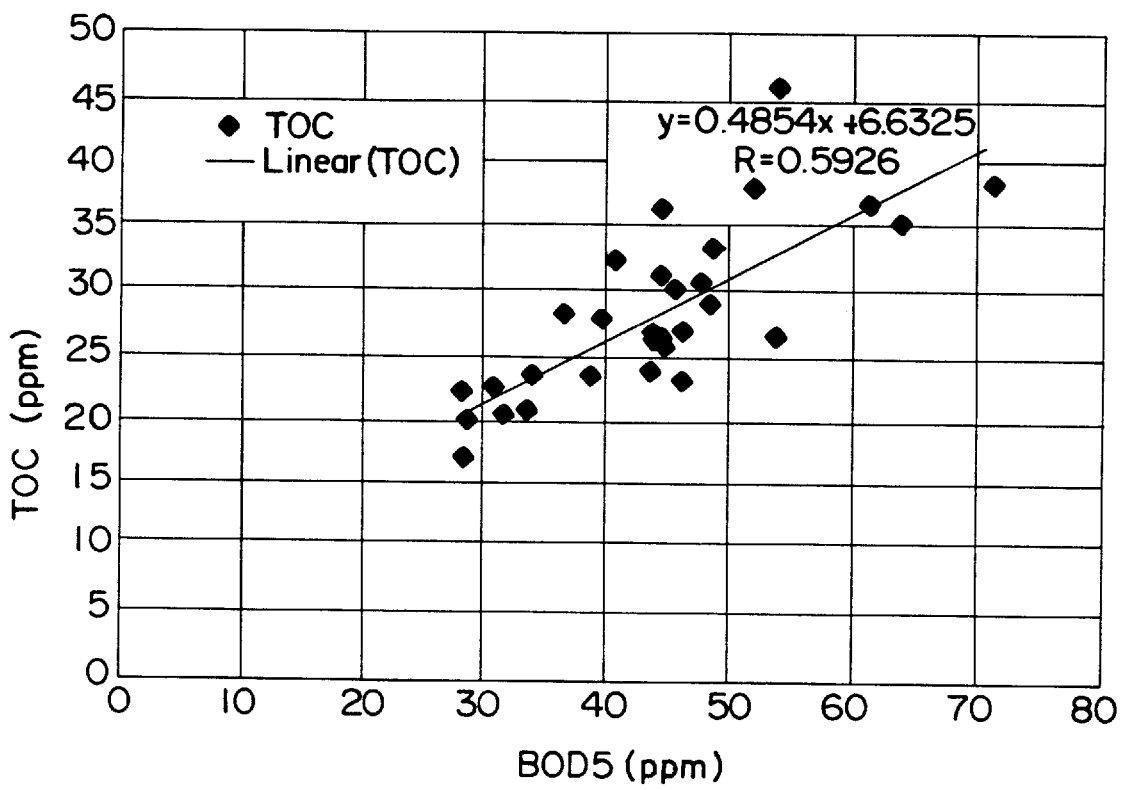
FIG. 6 is a graph showing the correlation of Total Organic Carbon (hereinafter referred to as "TOC") of the present invention with BOD5.
Figure 7:
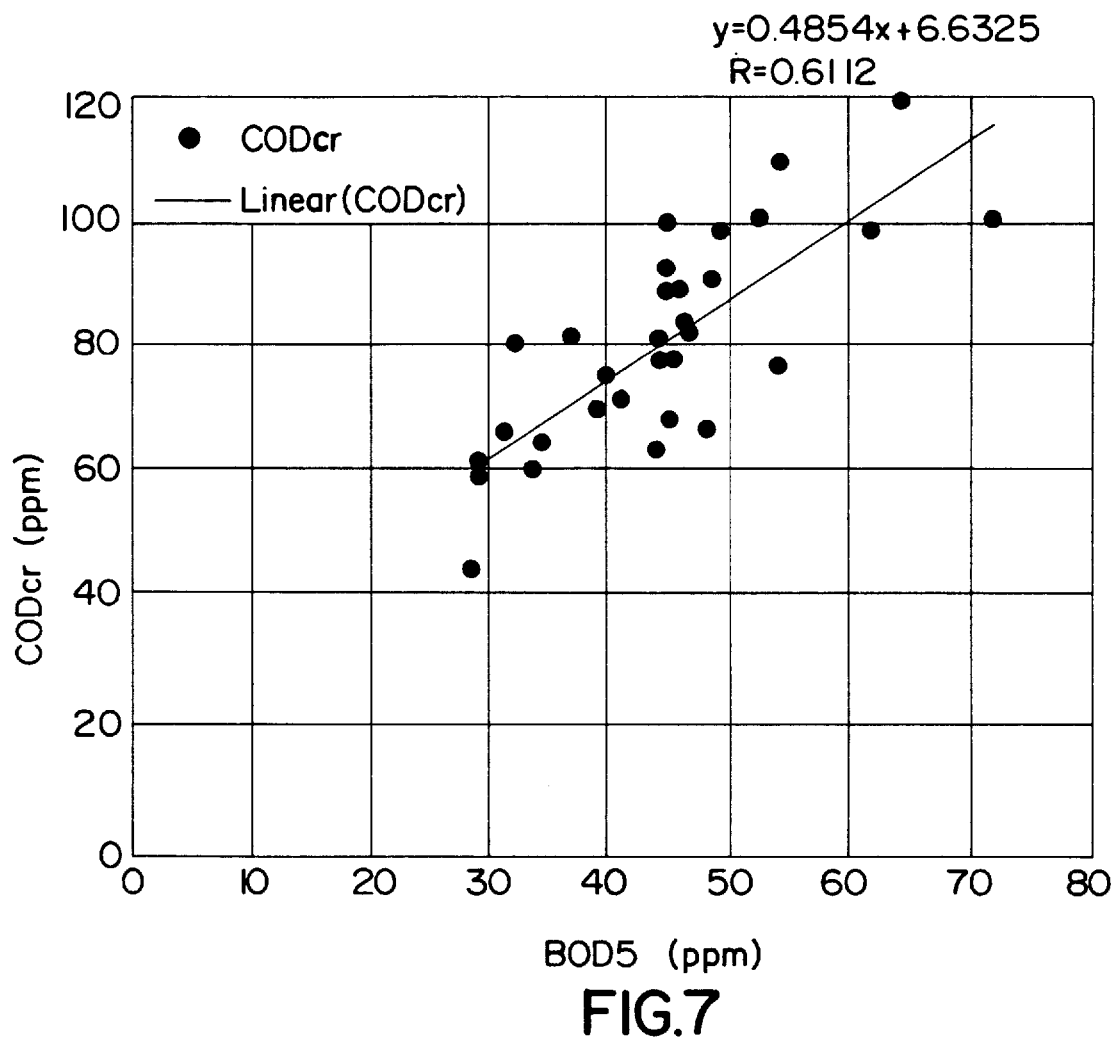
FIG. 7 is a graph showing the correlation of Chemical Oxygen Demand (hereinafter referred to as "COD") of the present invention with BOD5.

In order to understand the correlation with ease, the results are plotted for the same sample. As shown in FIGS. 5 to 7, the correlation coefficient with BOD5 is 0 79 for BODq, 0.59 for TOC, and 0.61 for COD. Thus, BODq is in the highest correlation with BOD5.

For influent water, measurement was made for one month in alternate mode. The results are given as shown in FIG. 5 below. The error rate, the deviation value divided by average value, is within 6%, which is better than that of discharge water.

TABLE 5

Error Rate of Influent Water

| Hour | Day 1st | 5th | 13th | 23th | 31st |
|---|---|---|---|---|---|
| 1 | | | | | |
| 2 | 52.3 | 65.3 | 78.9 | 72.1 | 81.5 |
| 3 | | | | | |
| 4 | 54.3 | 69.5 | 75.6 | 71.6 | 84.9 |
| 5 | | | | | |
| 6 | 54.5 | 67.8 | 78.9 | 69.5 | 89.4 |
| 7 | | | | | |
| 8 | 50.8 | 61.8 | 73.5 | 65.6 | 82.3 |
| 9 | | | | | |
| 10 | 54.6 | 66.9 | 69.9 | 79.2 | 81.2 |
| 11 | | | | | |
| 12 | 50.2 | 72.5 | 74.1 | 70.9 | 93.6 |
| 13 | | | | | |
| 14 | 56.0 | 67.8 | 76.8 | 68.8 | 87.5 |
| 15 | | | | | |
| 16 | 59.2 | 65.6 | 80.6 | 74.4 | 95.0 |
| 17 | | | | | |
| 18 | 51.3 | 62.7 | 84.5 | 72.9 | 85.6 |
| 19 | | | | | |
| 20 | 52.9 | 68.0 | 74.6 | 70.5 | 84.9 |
| 21 | | | | | |
| 22 | 50.1 | 61.3 | 71.5 | 64.2 | 88.2 |
| 23 | | | | | |
| Average | 53.3 | 66.3 | 76.3 | 70.9 | 86.7 |
| Deviation | 2.8 | 3.4 | 4.2 | 4.1 | 4.6 |
| Error Rate | 5.2 | 5.1 | 5.6 | 5.8 | 5.3 |

The present invention has been described in an illustrative manner, and it is to be understood the terminology used is intended to be in the nature of description rather than of limitation.

Many modifications and variations of the present invention are possible in light of the above teachings. Therefore, it is to be understood that within the scope of the appended claims, the invention may be practiced otherwise than as specifically described.

What is claimed is:

1. A continuous, quick BOD measurement method, comprising the steps of:

continuously culturing microorganisms in a reactor by introducing a mixture of a medium containing nutrients necessary for the growth of microorganisms and a sample water from a mixing bottle to the reactor at a controlled flow rate;

depleting all the organic materials available in the reactor by aerating the reactor without further introducing the medium and the sample in time;

measuring the endogenous respiration speed of the microorganisms which are in an endogenous respiration state owing to the depletion of the organic materials available;

feeding the sample from a sample tank to the reactor; and measuring the oxygen amount consumed by the microorganisms while they completely decompose the organic materials contained in the sample fed.

2. The continuous, quick BOD measurement method in accordance with claim 1, having a measurable range of 1–15,000 mg·BOD/L without using any diluent or buffer solution.

3. An apparatus for measuring BOD comprising:

a reactor on a magnetic stirrer, said reactor having an upper part and a bottom, said reactor being equipped with a temperature and dissolved oxygen sensor and a heater at its upper part, said reactor further provided with two openings at its bottom, said reactor containing microorganisms capable of decomposing organic materials, one of said openings serving as an inlet through which air is influxed into said reactor by the action of an air pump and the other opening serving as an inlet through which a sample water is fed into the reactor;

a sample tank having an upper part, sides and a bottom, said tank comprising a short tube at the tank upper part through which low concentration sample water is flowed into the sample tank, an overflow opening in the tank side for maintaining the water level of the sample, and an air conduit at the tank bottom for introducing air from the air pump;

a medium reservoir which stores the nutrients necessary for the growth of the microorganisms contained in the reactor;

a mixing bottle for mixing the sample water and the medium, said mixing bottle having an upper part, a side and a bottom, said mixing bottle comprising a first conduit in the mixing bottle side for introducing the medium from the medium reservoir by the action of a medium pump, a second conduit in the side of the mixing bottle for introducing the sample from the sample tank by the action of a sample pump during a measurement period, a third conduit in the mixing bottle upper part for introducing the sample from the sample tank by the action of a feeding pump during a culture period, and a discharge tube in the bottle bottom for discharging the influxes of the mixing bottle into the reactor;

an upper reaction bottle having an upper part, a side and a bottom, the upper reaction bottle comprising a neck at its bottom for connecting with the reactor, an opening in the reaction bottle upper part having a cap, and an opening in the reaction bottle side for draining the sample introduced from the reactor, said cap being provided with a level sensor, an air vent, and an inlet through which a high concentration sample is flowed into with the action of a syringe pump; and a microprocessor which controls all the operations necessary for automatic measurement.

4. The apparatus in accordance with claim 3, wherein said reactor contains porous carriers to which the microorganisms adhere to grow.

5. The apparatus in accordance with claim 3, wherein a glass tube with a diameter of 12 mm in which a plurality of pores 3.5 mm in diameter are present is inserted through said draining opening into said upper reaction bottle.

6. The apparatus in accordance with claim 3, wherein additional nutrients are provided to grow said microorganisms.

7. The apparatus in accordance with claim 3, wherein a helical baffle is provided within the neck of said upper reaction bottle, in order for liquid to easily move between said reactor and said upper reaction bottle.

8. The apparatus in accordance with claim 3, wherein said sample pump and said syringe pump are automatically chosen and controlled to add a suitable volume of said sample depending on the concentration of said sample.

9. An apparatus for measuring BOD comprising:

a reactor containing microorganisms capable of decomposing organic materials, said reactor comprising a container having an air inlet, a sample water inlet, and a temperature and dissolved oxygen sensor;

a sample tank having an inlet for receiving diluted sample water and an overflow for maintaining the sample water level in the tank;

a medium reservoir for storing nutrients for the growth of the microorganisms contained in the reactor;

a mixing bottle for mixing the sample water and the medium;

a series of conduits connected to said mixing bottle comprising a first conduit for transferring medium from the medium reservoir to the mixing bottle, and second and third conduits for introducing sample from the sample tank to the mixing bottle;

an upper reaction bottle comprising a first inlet connecting with the reactor, a second inlet through which concentrated sample is introduced, a first opening for draining sample, a second opening having a cap provided with a level sensor, and an air vent; and a microprocessor which controls the operation of the apparatus.

10. An apparatus for measuring BOD comprising:

a reactor containing microorganisms capable of decomposing organic materials, said reactor comprising a container having an air inlet, a sample water inlet, and a temperature and dissolved oxygen sensor;

a sample tank having an inlet for receiving diluted sample water;

a medium reservoir for storing nutrients for the growth of the microorganisms contained in the reactor;

a mixing bottle for mixing the sample water and the medium;

a series of conduits connected to said mixing bottle comprising a first conduit for channeling medium from the medium reservoir to the mixing bottle, a second conduit for channeling sample from the sample tank to the mixing bottle, and a discharge conduit for channeling medium from the mixing bottle to the reactor;

an upper reaction bottle comprising a first inlet connecting with the reactor, a second inlet through which concentrated sample is introduced, an opening for draining sample, a cap provided with a level sensor, and an air vent; and a microprocessor which controls the operation of the apparatus.

* * * * *